US009173371B2

(12) United States Patent
Nielsen et al.

(10) Patent No.: US 9,173,371 B2
(45) Date of Patent: Nov. 3, 2015

(54) TOBACCO COMPOSITIONS AND METHODS OF MAKING (75) Inventors: Mark T. Nielsen, Nicholasville, KY (US); Marcos F. Lusso, Lexington, KY (US); Francis Antoine, Winchester, KY (US)

(73) Assignee: U.S. Smokeless Tobacco Company, Richmond, VA (US)

( * ) Notice: Subject to any disclaimer, the term of this patent is extended or adjusted under 35 U.S.C. 154(b) by 612 days.

(21) Appl. No.: 13/442,203

(22) Filed: Apr. 9, 2012

(65) Prior Publication Data

US 2012/0216309 A1 Aug. 23, 2012

Related U.S. Application Data (63) Continuation of application No. 12/036,033, filed on Feb. 22, 2008, now Pat. No. 8,168,855.

(60) Provisional application No. 60/891,435, filed on Feb. 23, 2007, provisional application No. 60/991,579, filed on Nov. 30, 2007.

(51) Int. Cl.
*A01H 1/04* (2006.01)
*A01H 5/12* (2006.01)
*A01H 1/00* (2006.01)
*A24B 15/10* (2006.01)

(52) U.S. Cl.
CPC .. *A01H 5/12* (2013.01); *A01H 1/00* (2013.01); *A24B 15/10* (2013.01)

(58) Field of Classification Search
None
See application file for complete search history.

(56) References Cited

U.S. PATENT DOCUMENTS

| 3,845,774 | A | 11/1974 | Lowe et al. |
| 4,528,993 | A | 7/1985 | Sensabaugh, Jr. et al. |
| 4,606,357 | A | 8/1986 | Dusek et al. |
| 4,607,646 | A | 8/1986 | Lilly, Jr. et al. |
| 4,660,577 | A | 4/1987 | Sensabaugh et al. |
| 4,848,373 | A | 7/1989 | Lenkey |
| 4,987,907 | A | 1/1991 | Townend |
| 5,073,677 | A | 12/1991 | Helmer et al. |
| 5,331,981 | A | 7/1994 | Tamaoki et al. |
| 5,372,149 | A | 12/1994 | Roth et al. |
| 8,168,855 | B2 | 5/2012 | Nielsen et al. |
| 2004/0084056 | A1 | 5/2004 | Lawson et al. |
| 2004/0118421 | A1 | 6/2004 | Hodin et al. |
| 2004/0118422 | A1 | 6/2004 | Lundin et al. |
| 2005/0115580 | A1 | 6/2005 | Quinter et al. |
| 2005/0121046 | A1 | 6/2005 | Hempfling et al. |
| 2005/0132444 | A1 | 6/2005 | Xu |
| 2005/0178398 | A1 | 8/2005 | Breslin et al. |
| 2005/0223442 | A1 | 10/2005 | Xu |
| 2005/0244521 | A1 | 11/2005 | Strickland et al. |
| 2006/0037096 | A1 | 2/2006 | Xu |
| 2006/0037623 | A1 | 2/2006 | Lawrence, Jr. |
| 2006/0041949 | A1 | 2/2006 | Xu et al. |
| 2006/0185686 | A1 | 8/2006 | Lawrence, Jr. |
| 2006/0191548 | A1 | 8/2006 | Strickland et al. |
| 2007/0137663 | A1 | 6/2007 | Taylor et al. |
| 2007/0199097 | A1 | 8/2007 | Xu et al. |

FOREIGN PATENT DOCUMENTS

| CN | 85101482 | 8/1986 |
| JP | 558-155070 A | 9/1983 |
| JP | 558-157704 A | 9/1983 |
| JP | H09-224639 A | 9/1997 |
| JP | 2006-504430 A | 2/2006 |
| JP | 2008-538911 A | 11/2008 |
| WO | WO 2005/046363 | 5/2005 |
| WO | WO 2005/111217 | 11/2005 |
| WO | WO 2006/022784 | 3/2006 |
| WO | WO 2006/091194 | 8/2006 |

OTHER PUBLICATIONS

Nielsen, M. et al. Crop Science 1992; vol. 32, pp. 1148-1150.*
Nielsen, M., Tobacco Science, 1991; vol. 35, pp. 69-73.*
Johnson, M. et al. Phytopathology, 1982; pp. 68-71.*
"Tobacco in the United States," 1979, U.S. Department of Agriculture, Agricultural Marketing Service, Misc. Publication No. 867, pp. 1-27.
"PI 119461" USDA, ARS, National Genetic Resources Program, Germplasm Resources Information Network—(GRIN) National Germplasm Resources Laboratory, Beltsville, MD, Jan. 1937, Retrieved from the Internet: URL: http://www.ars-grin.gov/cgi-bin/npgs/acc/display.pl?1131903> [retrieved on May 28, 2005].
"PI 404936" USDA, ARS, National Genetic Resources Program, Germplasm Resources Information Network—(GRIN) National Germplasm Resources Laboratory, Beltsville, MD, Oct. 22, 1975, Retrieved from the Internet: URL: http://www.ars-grin.gov/cgi-bin/npgs/acc/display.pl?1305041> [retrieved on May 28, 2010].
"PI 405590" USDA, ARS, National Genetic Resources Program, Germplasm Resources Information Network—(GRIN) National Germplasm Resources Laboratory, Beltsville, MD, Oct. 22, 1975, Retrieved from the Internet: URL: http://www.ars-grin.gov/cgi-bin/npgs/acc/display.pl?1305522> [retrieved on May 31, 2010].
"PI 408940" USDA, ARS, National Genetic Resources Program, Germplasm Resources Information Network—(GRIN) National Germplasm Resources Laboratory, Beltsville, MD, May 19, 1976, Retrieved from the Internet: URL: http://www.ars-grin.gov/cgi-bin/npgs/acc/display.pl?1308371> [retrieved on May 31, 2010].
Adams, *Characterization and measurement of flavor compounds*, 1985, by Bills & Mussinan (eds.), ACS Symposium Series 289, American Chemical Society, Washington DC, pp. 11-25.
Arrendale et al., "Characterization of the sucrose ester fraction from *nicotiana glutinosa*," *J. Agric. Food. Chem.*, 1990, 38:75-85.
Belitz and Grosch, "Amino Acids" and "Peptides," *Food Chemistry*, 1999, pp. 33-37 & 763-764.

(Continued)

*Primary Examiner* — Russell Kallis
(74) *Attorney, Agent, or Firm* — Fish & Richardson P.C.

(57) ABSTRACT

The present disclosure describes tobacco varieties having reduced levels of DVTs, methods of making such varieties, and tobacco compositions including such varieties.

11 Claims, 6 Drawing Sheets

(56) References Cited

OTHER PUBLICATIONS

Burton et al., "Changes in Chemical Composition of Burley Tobacco During Senescence and Curing. 2. Acylated Pyridine Alkaloids," *J. Agric. Food Chem.*, 1988, 38(3):579-583.
Burton et al., "Distribution of Tobacco Constituents in Tobacco Leaf Tissue. 1. Tobacco-Specific Nitrosamines, Nitrate, Nitrite, and Alkaloids," *J. Agric. Food Chem.*, 1992, 40:1050-1055.
Bush, "Alkaloid Biosynthesis," *Tobacco, Production, Chemistry and Technology*, 1999, Davis & Nielsen (eds.), Ch. 8, Blackwell Publishing, Oxford, pp. 285-291.
Chang and Grunwald, "Duvatrienediols in cuticular wax of Burley tobacco leaves," *J. Lipid Res.*, 1976, 17:7-11.
Dunkel et al., "Molecular and sensory characterization of gamma-glutamyl peptides as key contributors to the kokumi taste of edible beans (*Phaseolus vulgaris* L.)," *J. Agric. Food Chem.*, 2007, 55:6712-6719.
Enzell, "Terpenoid components of leaf and their relationship to smoking quality and aroma," *Recent Adv. Tob. Sci.*, 1976, 6:32-60.
Grub, *Flavourings*, 1998, by Ziegler & Ziegler (eds.), pp. 513-524, Wiley-VCH Verlag GmbH, Weinheim, Germany.
Guo and Wagner, "Biosynthesis of labdenediol and sclareol in cell-free extracts from trichomes of *nicotiana glutinosa*," *Planta*, 1995, 197:627-632.
Guo et al., "Biosynthesis of the diterpene cis-abienol in cell-free extracts of tobacco trichomes," *Arch. Biochem. Biophys.*, 1994, 308:103-108.
Johnson et al., "Inheritance of Glandular Trichomes in Tobacco," *Crop Sci.*, 1988, 28:241-244.
Johnson et al., "Evaluation of Tobacco Introduction 1406 as a Source of Virus Resistance," *Phytopathology*, 1982, 72:68-71.
Koelle, "Genetische Analyse einer Y-virus-(Rippenbraune) resistenten Mutante der Tabaksorte virgin A," *Der Zauchter*, 1961, 31:71-72 (including English summary).
Lawless and Gillette, *Characterization and measurement of flavor compounds*, 1985, by Bills & Mussinan (eds.), ACS Symposium Series 289, American Chemical Society, Washington DC, pp. 26-41.
Leffingwell, "Leaf Chemistry Basic Chemical Constituents of Tobacco Leaf and differences among Tobacco Types," *Tobacco, Production, Chemistry and Technology*, 1999, Davis & Nielsen (eds.), Ch. 8, Blackwell Publishing, Oxford, pp. 265-284.
Meilgaard et al., *Sensory evaluation techniques*, 1991, 2nd Ed., CRC Press, Boca Raton, FL (TOC Only).
Miller, "A Burley Tobacco Resistant to TVMV, TEV, and PVY," Bulletin 657 from University of Tennessee re TN86, Oct. 1987.
Nielsen and Severson, "Variation of flavor Components on Leaf Surfaces of Tobacco Genotypes Differing in Trichome Density," *J. Agric. Food Chem.*, 1990, 38:467-471.
Nielsen and Severson, "Inheritance of a Diterpene Constituent in Tobacco Trichome Exudate," *Crop Sci.*, 1992, 32:1148-1150.
Nielsen et al., "Comparative Ultrastructural Features of Secreting and Nonsecreting Glandular Trichomes of two Genotypes of *Nicotiana Tabacum* L." *Bot. Gaz.*, 1991, 152(1):13-22.
Nielsen et al., "Inheritance Pattern for Secreting and Nonsecreting glandular Trichomes in Tobacco," *Crop Science*, 1982, 22:1051-1053.
Nielsen, "Altering flavor and Aroma Constituents of Burley Tobacco," *Tobacco Science*, 1991, 35:59-73.
Nielsen, "Registration of KDH 926, KDH 926, KDH 960 Tobacco Gerplasm Lines With Different Levels of Trichome Exudate Constituents," *Crop Sci.*, 1989, 29:1584-1585.

Peele et al., "Chemical and Biochemical Changes During the Flue-Curing of Tobacco," *Rec. Adv. Tob. Sci.*, 1996, 21:81-133
Poehlman, *Breeding Field Crops*, 1987, 3d. supp. ed., Van Nostrand Reinhold, New York (TOC Only).
Reid and Haley, "Studies on the Fermentation of Tobacco 1. The Microflora of Cured and Fermenting Cigar-leaf Tobacco," *Bulletin 356*, 1938, Pennsylvania Agricultural Experiment Station, State College, PA.
Severson et al., "Cuticular Constituents of Tobacco: Factors Affecting Their Production and Their Role in Insect and Disease Resistance and Smoke quality," *Recent Advances In Tobacco Science*—Highlights of Current Chemical Research on Tobacco Composition, 39th Tobacco Chemists' Research Conference, Oct. 2-5, 1985, Montreal, Quebec, Canada pp. 105-200.
Severson et al., "Isolation and characterization of the sucrose esters of the cuticular waxes of green tobacco leaf," *J. Agric. Food Chem.*, 1985, 33:870-875.
Smeeton, "Genetic control of tobacco quality," *Rec. Adv. Tob. Sci.*, 1987, 13:3-26.
Tamura et al., "An enhancing effect on the saltiness of sodium chloride of added amino acids and their esters," *Agric. Biol. Chem.*, 1989, 53:1625-1633.
Tso, *Tobacco, Production, Chemistry and Technology*, 1999, Chapter 1, Davis & Nielsen (eds.), Blackwell Publishing, Oxford.
Wagner, "Leaf Surface chemistry," *Tobacco, Production, Chemistry and Technology*, 1999, Davis & Nielsen (eds.), Ch. 8, Blackwell Publishing, Oxford, pp. 292-303.
Wahlberg and Eklund, "Cembranoids, Pseudopteranoids, and Cubitanoids of Natural Occurrence," *Fortschritter der Chemi Organischer Natursfotte*, 1992, Herz et al. (eds.), 59:141-294, Springer Verlag, NY.
Wang et al., "Suppression of a P450 hydroxylase gene in plant trichome glands enhances natural-products-based aphid resistance," *Nature Biotechnology*, 2001, 19:371-374.
Weeks et al., "Differences in Aroma, Chemistry, Solubilities, and Smoking Quality of Cured Flue-cured Tobaccos with Aglandular and Glandular Trichomes," *J. Agric. Food Chem.*, 1992, 40:1911-1916.
Weeks, "Relationship between Leaf Chemistry and Organoleptic Properties of Tobacco Smoke," *Tobacco, Production, Chemistry and Technology*, 1999, Davis & Nielsen (eds.), Ch. 8, Blackwell Publishing, Oxford, pp. 304-312.
Wiernik et al., "Effect of Air-Curing on the Chemical Composition of Tobacco," *Rec. Adv. Tob. Sci.*, 1996, 21:39-80.
Wolf, "Production, in Venezuela, of Indigenous Varieties of Tobacco," *Economic Botany*, 1949, 3(2):132-139.
Authorized Officer Simin Baharlou, International Preliminary Report on Patentability in PCT/US2008/054769 mailed Sep. 3, 2009, 8 pages.
Supplementary European Search Report in EP 08 73 0552 mailed Jul. 1, 2010, 11 pages.
International Search Report and Written Opinion for PCT/US2008/054769 mailed Jul. 11, 2008, 10 pages.
Brown & Williamson Tobacco Corporation, "Subjective Evaluation of Some Diterpenoids," Mar. 16, 1982, 1 page.
Hamada, et al. "Potato Virus Y-resistant Mutation Induced by the Combination Treatment of Ion beam Exposure and Anther Culture in *Nicotiana tabacum* L.," Plant Biotechnology, 16(4), 285-289, Sep. 1, 1999.
Nakakawaji "Genetic Relationship between Duvatrienediol Content and Resistance to Potato Virus Y strain T" Bulletin of the Leaf Tobacco Research Laboratory, 6:51-58, 1996.

* cited by examiner

TOBACCO COMPOSITIONS AND METHODS OF MAKING

CROSS REFERENCE TO RELATED APPLICATIONS

This application is a Continuation of, and claims benefit under 35 U.S.C. §120 to, U.S. application Ser. No. 12/036,033 filed Feb. 22, 2008, which claims benefit under 35 U.S.C. §119(e) to U.S. Application No. 60/891,435 filed Feb. 23, 2007 and U.S. Application No. 60/991,579 filed Nov. 30, 2007, all of which are incorporated herein in their entirety.

TECHNICAL FIELD

This disclosure relates to tobacco plants and smokeless tobacco compositions, and more particularly to tobacco plants that exhibit reduced levels of 4,8,13-duvatriene-1,3-diols (DVTs) and methods of making and using such plants.

BACKGROUND

Smokeless tobaccos products are orally consumed without subjecting the product to combustion. These products are manufactured in a variety of forms including chewing tobacco, dry snuff and moist snuff. Generally, these types of products are made as follows with the steps being in no particular order: cutting or grinding the tobacco into a suitable size; dipping or spraying the tobacco with a casing solution; partially drying the cased tobacco; holding the tobacco in containers for a period of time; and packaging the tobacco. See, for example, U.S. Pat. Nos. 4,528,993; 4,660,577; and 4,987,907.

Some smokeless tobacco products may have organoleptic properties that do not appeal to some consumers. To provide a variety of products with different taste characteristics, chewing tobacco and snuffs are often treated with a variety of flavorants and other flavor enhancing materials. However, the addition of flavors may not be appealing to certain consumers. The inclusion of flavors almost always requires additional processing steps when producing the smokeless tobacco products (see, for example, U.S. Publication No. 2005/0115580). Accordingly, a need exists for tobacco that can provide oral satisfaction by delivering alternative flavor profiles.

SUMMARY

This disclosure describes tobacco varieties having reduced levels of 4,8,13-duvatriene-1,3-diols (DVTs), also referred to as 4,8,13-cembratriene-1,3-diols. This disclosure also describes methods of making such varieties and methods of using such varieties. Varieties that exhibit reduced levels of DVTs exhibit flavor profiles that may appeal to some consumers.

In one aspect, a smokeless tobacco composition is provided that includes cured tobacco having reduced levels of DVTs relative to cured tobacco of the variety designated KY14. In another aspect, a smokeless tobacco composition is provided that includes cured tobacco, the cured tobacco prepared from green tobacco having less than 20 µg of DVT per $cm^2$ of green leaf tissue. In another aspect, a smokeless tobacco composition is provided that includes cured tobacco from a variety selected for reduced levels of DVTs, plants of the variety having less than 20 µg of DVTs per $cm^2$ of green leaf tissue. In one embodiment, the cured tobacco is from a variety selected from the group consisting of TI 1406, TI 1269, GR139NS, KDH959, and progeny thereof having reduced levels of DVTs relative to cured tobacco of the variety designated KY14 and progeny thereof having less than 20 µg of DVT per $cm^2$ of green leaf tissue.

In one embodiment, the cured tobacco exhibits significantly reduced bitterness in a sensory panel evaluation relative to cured tobacco of the variety designated KY14. Generally, the cured tobacco or the green tobacco also has reduced levels of solanone, solavetivone, cembrene, or thunbergol. In certain embodiments, the cured tobacco is dark fire-cured tobacco, dark air-cured tobacco, Burley air-cured tobacco other than from a variety designated TI 1406, flue-cured tobacco, or sun-cured tobacco. Representative compositions include, for example, a moist smokeless tobacco, a dry smokeless tobacco, a chewing tobacco, a smokeless cigarette, an edible film, an extruded product, a tablet, or a tobacco-coated toothpick.

In one aspect, a method of producing a plant variety is provided. Such methods include the steps of: crossing first tobacco plants with second tobacco plants to produce progeny plants, wherein the first tobacco plants have less than 20 µg DVTs/$cm^2$ green leaf tissue; allowing the progeny plants to self-pollinate for at least one generation; and selecting, in at least one generation, for reduced levels of DVTs in tobacco relative to tobacco of the variety designated KY14, selecting for less than 20 µg of DVT per $cm^2$ of green leaf tissue or selecting for significantly reduced bitterness in a sensory panel evaluation of tobacco from plants of the generation, thereby producing the variety.

In another aspect, methods of producing a plant variety are provided. Such methods include the steps of: mutagenizing tobacco plant tissue; propagating plants derived from the mutagenized plant tissue by self-pollination for at least one generation; and selecting, in at least one generation, for reduced levels of DVTs in tobacco relative to tobacco of the variety designated KY14, selecting for less than 20 µg of DVT per $cm^2$ of green leaf tissue or selecting for significantly reduced bitterness in a sensory panel evaluation of tobacco from plants of the generation, thereby producing the variety.

In still another aspect, methods of producing a plant variety are provided. Such methods include the steps of: crossing first tobacco plants with second tobacco plants to produce progeny plants, the first tobacco plants having significantly reduced bitterness in a sensory panel evaluation of tobacco from the plants, relative to tobacco of the variety designated KY14; allowing the progeny plants to self-pollinate for at least one generation; and selecting, in at least one generation, for reduced levels of DVTs in tobacco relative to tobacco of the variety designated KY14, selecting for less than 20 µg of DVT per $cm^2$ of green leaf tissue or selecting for significantly reduced bitterness in a sensory panel evaluation of tobacco from plants of the generation, thereby producing the variety.

Tobacco plants or varieties produced by the methods disclosed herein also are provided. Such plants or varieties typically have less than 20 µg of DVTs per $cm^2$ green leaf tissue.

In one aspect, cured *N. tabacum* tobacco is provided having reduced levels of DVTs, provided that the tobacco is not produced from a variety shown in Table 1. In another aspect, cured tobacco is provided that is produced from plants of a tobacco variety selected for reduced levels of DVTs in green leaf tissue. In still another aspect, cured tobacco is provided that is produced from plants of a tobacco variety selected for significantly reduced bitterness in a sensory panel evaluation.

In one aspect, methods of preparing tobacco having reduced bitterness are provided. Such methods include the steps of: curing fresh tobacco; aging cured tobacco; and washing the fresh tobacco, the cured tobacco, or the aged and cured tobacco with a food-grade solvent. A representative food-grade solvent is ethanol. In certain embodiments, the washed tobacco exhibits significantly reduced bitterness in a sensory panel evaluation and in certain embodiments, the fresh tobacco does not exhibit significantly reduced bitterness in a sensory panel evaluation. Cured tobacco having significantly reduced bitterness in a sensory panel evaluation is provided that is produced by such a method. Such cured tobacco is produced from fresh tobacco having less than 20 μg of DVTs per cm$^2$ of green leaf tissue.

Unless otherwise defined, all technical and scientific terms used herein have the same meaning as commonly understood by one of ordinary skill in the art to which this invention belongs. Although methods and materials similar or equivalent to those described herein can be used in the practice of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1 is an image of a thin layer chromatography (TLC) plate of leaf surface compounds from a number of tobacco varieties.

DETAILED DESCRIPTION

This disclosure describes tobacco that has reduced levels of 4,8,13-duvatriene-1,3-diols (DVTs) when compared to, for example, tobacco from a variety designated KY14. Thus, the present disclosure describes tobacco varieties having reduced levels of DVTs, methods of making such varieties, and tobacco compositions including such varieties. It has been discovered that smokeless tobacco compositions made from tobacco having reduced levels of DVTs have unique organoleptic profiles, since DVTs have been found by the inventors to be associated with the organoleptic characteristic of bitterness.

DVTs are cembranoids, which are a class of monocyclic diterpenoids found in the leaf surface trichome exudates of the five main types of tobacco: dark, Virginia, Burley, Oriental and cigar. Cembranoids and their derivatives are produced in the glandular heads of trichomes on the leaf surface and are part of the surface cuticular waxes where they can be found along with sugar esters, wax hydrocarbons, esters and alcohols. More than 70 different cembranoids have been identified from tobacco along with more than 60 different compounds related to cembranoids (e.g., compounds produced by biodegradation, oxidative processes and retro-aldol reactions of cembranoids). In addition to DVTs, other cembranoids or compounds related to cembranoids include, but are not limited to, solavetivone, cembrene, thunbergol, solanol, norsolanadione, and solanascone. For a review of cembranoids and related compounds, see, for example, Wahlberg & Eklund (1992, 'Cembranoids, Pseudopteranoids, and Cubitanoids of Natural Occurrence,' in *Fortschritter der Chemi Organischer Natursfotte*, Herz et al., eds., 59:141-294, Springer Verlag, NY) and Leffingwell (1999, 'Leaf Chemistry,' in *Tobacco, Production, Chemistry and Technology*, Davis & Nielsen, eds., Ch 8, Blackwell Publishing, Oxford).

Tobacco and tobacco varieties having reduced levels of DVTs generally exhibit less than 20 μg DVTs per cm$^2$ of green leaf tissue (e.g., less than 19, 18, 16, 15, 14, 12, 10, 8, 6, 5, 4, 3, 2, or 1 μg DVTs/cm$^2$), measured by the method described in Nielsen & Severson (1990, *J. Agric. Food Chem.*, 38:467-471). Exemplary species of *Nicotiana* that are reported to have reduced levels of DVTs include *N. accuminata*, *N. africana*, *N. alata*, *N. debneyi*, *N. glauca*, *N. knightiana*, *N. langsdorfii*, *N. longiflora*, *N. megalosiphon*, *N. paniculata*, *N. plumbaginifolia*, *N. repanda*, *N. rustica*, and *N. sanderae*, and representative tobacco varieties having less than 20 μg DVTs per cm$^2$ of green leaf tissue (i.e., reduced levels of DVTs) include, without limitation, TI 1406, GR139NS, TI 1269 and KDH959. Other tobacco varieties from that are suitable for use in the methods disclosed herein can be found, for example, in the USDA *Nicotiana* Germplasm Collection (available online at ars-grin.gov/npgs on the World Wide Web). Table 1 shows representative varieties of *N. tabacum* from the USDA *Nicotiana* Germplasm Collection having reduced levels of DVTs.

TABLE 1

| Low-DVT Varieties | |
|---|---|
| Tobacco | μg DVTs/cm$^2$ green leaf |
| TI 1004 | 14.06 |
| TI 1024 | 0.40 |
| TI 1029 | 0.31 |
| TI 1030 | 0.1 |
| TI 1031 | 0 |
| TI 1032 | 0.24 |
| TI 1070 | 8.7 |
| TI 1078 | 11.35 |
| TI 1112 | 0.19 |
| TI 1113 | 1.07 |
| TI 1117 | 0.71 |
| TI 1120 | 0.05 |
| TI 1123 | 0.04 |
| TI 1124 | 0.56 |
| TI 1227 | 9.81 |
| TI 1269 | 0.49 |
| TI 1349 | 3.06 |
| TI 1391 | 4.94 |
| TI 1406 | 0.46 |
| TI 1442 | 13.38 |
| TI 1448 | 10.7 |
| TI 1449 | 2.06 |
| TI 1524 | 0.17 |
| TI 1533 | 14.6 |
| TI 1535 | 8.96 |

TABLE 1-continued

Low-DVT Varieties

| Tobacco | μg DVTs/cm² green leaf |
|---|---|
| TI 490 | 10.29 |
| TI 538 | 0.44 |
| TI 717 | 11.78 |
| TI 870 | 0.31 |
| TI 70 | 0.16 |
| KDH959 | 3.5 |
| KDH950 | 0.7 |
| Barinas | 0.24 |
| Badischer Burley E | 9.33 |

The amount of DVTs is considered to be reduced in a plant when the reduction in the amount of DVTs is statistically significant when compared to the amount of DVTs in a control plant. A 'statistically significant' reduction in DVTs refers to a p-value of less than 0.10, e.g., a p-value of less than 0.05, a p-value of less than 0.025 or a p-value of less than 0.01, using an appropriate parametric or non-parametric statistic, e.g., Chi-square test, Student's t-test, Mann-Whitney test, or F-test. A suitable control plant is *Nicotiana tabacum* variety KY14 (PI 552477). Other suitable control tobacco plants include those plants that are comparable to KY14, KY171, or those that have a DVT level of from greater than about 20 to about 100 μg DVTs/cm² green leaf tissue. Such control plants are publicly available and can be obtained from, for example, the USDA *Nicotiana* Germplasm Collection or the National Seed Storage Laboratory (Ft. Collins, Colo.).

DVTs can be obtained, identified and/or measured using methods routine in the art. DVTs are analyzed from leaves that are around 15-25 cm in length. Generally, leaves around 20 cm in length are selected and are harvested when the plant begins to flower (e.g., when the first flower is open or when one or more buds have opened). DVTs can be removed from the surface of the leaves by washing the leaves with a solvent such as acetonitrile, methylene chloride, acetone or chloroform. The trimethysilyl derivatives of the monocyclic diterpenoids then can be separated, identified and quantitated using, for example, GC or GC/MS. See Arrendale et al. (1990, *J. Agric. Food. Chem.*, 38:75-85) and Severson et al. (1985, *J. Agric. Food Chem.*, 33:870-75). Generally, acetonitrile preferentially removes diterpenes and sugar esters, while the other less polar solvents remove hydrocarbons in addition to the diterpenes and sugar esters. Alternatively, separation without derivatizing the DVTs can be performed using HPLC (see, e.g., Guo & Wagner (1995, *Planta*, 197:627-32); Guo et al. (1994, *Arch. Biochem. Biophys.*, 308:103-8)). In addition to GC, GC/MS, and HPLC, thin layer chromatography (TLC) methods also can be used to separate or partially separate DVTs from other cembranoids. Representative TLC conditions are disclosed herein in the Examples.

Tobacco varieties having reduced levels of DVTs and tobacco compositions containing such low-DVT tobacco exhibits improved flavor characteristics in sensory panel evaluations when compared to tobacco or tobacco compositions that do not have reduced levels of DVTs. The flavor characteristics of tobacco or a tobacco composition containing such tobacco can be evaluated by a sensory panel using techniques known in the art. For example, panelists can be trained and used to evaluate the flavor characteristics of tobaccos according to Grub (1998, In *Flavourings* by Ziegler & Ziegler, eds., pp. 513-524, Wiley-VCH Verlag GmbH, Weinheim, Germany); Tamura et al. (1989, *Agric. Biol. Chem.*, 53, 1625-1633); and Dunkel et al. (2007, *J. Agric. Food Chem.*, 55:6712-9). In addition, North Carolina State University Sensory Service Center, The Institute for Sensory Research at Syracuse University, Ohio State University Sensory Science Group, the Sensory Laboratory at Oregon State University and Monell Chemical Senses Center in Philadelphia have sensory testing facilities and offer various sensory evaluation services.

The present disclosure describes tobacco and tobacco varieties having reduced levels of DVTs and methods of making such plants. By "tobacco" is meant any part, e.g., leaves, flowers, roots, and stems, of any member of the genus *Nicotiana*. Exemplary species of tobacco include *N. rustica*, *N. tabacum*, *N. tomentosiformis*, *N. sylvestris*, and *N. glauca*. As used herein, a "variety" is a group of plants that display little or no genetic variation between individuals for at least one trait. Tobacco varieties that can be used in the methods described herein can be from the fire-cured and dark air-cured classes, however, varieties from the flue-cured or light air-cured classes also can be used. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972, on Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Varieties can be obtained, for example, by the selection of a natural or induced mutant, a variant individual from plants of the initial variety, self-pollination and/or backcrossing, transformation, or vegetative propagation.

In one embodiment, a species of tobacco or a tobacco variety having reduced levels of DVTs can be generated by crossing a variety having reduced levels of DVTs with plants of a second variety (e.g., an existing tobacco variety). The second variety can be, for example, an agronomically elite variety exhibiting, for example, desirable crop traits including, but not limited to, high yield, disease resistance, drought tolerance, sugar content, leaf size, leaf width, leaf length, leaf quality, leaf color, leaf reddening, leaf yield, internode length, flowering time, lodging resistance, stalk thickness, high grade index, curability, curing quality, mechanical harvestability, holding ability, height, maturation, stalk size, and leaf number per plant. Methods of crossing plants are well known in the art and include, without limitation, hand pollination of female stigma from one variety with pollen from a second variety.

The F1 progeny plants resulting from such a cross can be backcrossed or self-pollinated. For example, F1 progeny can be allowed to self-pollinate for at least one generation (e.g., one, two, three, four, five or six generations) and/or F1 progeny plants can be backcrossed to one of the parents (e.g., BC1, BC2, BC3, and subsequent generation plants). Progeny refers to descendants from a cross between particular plants or plant varieties, e.g., seeds developed on a particular plant. Progeny also include seeds formed on F2, F3, and subsequent generation plants. Other breeding techniques also can be used to make a tobacco variety having reduced levels of DVTs. Such methods include, but are not limited to, single seed descent, production of dihaploids, pedigree breeding and recombinant technology using transgenes. The progeny plants resulting from any such crosses can be screened for the level of DVTs. See, for example, Johnson et al., 1988, *Crop Sci.*, 28:241, which is incorporated herein by reference.

Alternatively, an existing tobacco variety (e.g., a tobacco variety that does not have reduced levels of DVTs) can be mutagenized using methods known in the art. Mutations can be induced in living organisms or in cultured cells by a variety of mutagens, including ionizing radiation, ultraviolet radiation, or chemical mutagens, by infection with certain viruses which integrate into the host genome, or by the introduction of nucleic acids previously mutagenized in vitro. Plants regenerated from mutagenized plants or plant cells can be allowed to self-pollinate and the progeny then screened for those plants having a reduced level of DVTs.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful.

Plants produced by any of the methods described herein (e.g., breeding, mutagenesis) can be evaluated for the levels of DVTs and/or bitterness using a number of different approaches. For example, the level of DVTs can be determined by extracting and separating the leaf-surface compounds as described herein. In some instances, the level of DVTs in a plant can be compared, directly or indirectly, to one or more control plants. In addition or alternatively, the bitterness of a tobacco leaf (green or cured) can be evaluated by a sensory panel as described herein. Plants identified as having reduced levels of DVTs can be selected for further propagation.

Seed from tobacco plants that have been identified as having reduced levels of DVTs can be planted in the field, harvested and further processed using methods standard in the art. For example, green leaf tobacco having reduced levels of DVTs can be cured using conventional means, e.g., flue-cured, fire-cured, air-cured or sun-cured. See, for example, Tso (1999, Chapter 1 in *Tobacco, Production, Chemistry and Technology*, Davis & Nielsen, eds., Blackwell Publishing, Oxford) for a description of different types of curing methods. In addition, the changes in tobacco chemistry that result from different methods of curing have been well studied. See, for example, Peele et al. (1996, *Rec. Adv. Tob. Sci.*, 21:81-133) and Wiernik et al. (1996, *Rec. Adv. Tob. Sci.*, 21:39-80).

In some embodiments, cured tobacco having reduced levels of DVTs can be conditioned and/or fermented. Conditioning includes, for example, a heating, sweating or pasteurization step as described in U.S. Publication Nos. 2004/0118422 or 2005/0178398. Fermenting typically is characterized by high initial moisture content, heat generation, and a 10 to 20% loss of dry weight. See, e.g., U.S. Pat. Nos. 4,528,993, 4,660,577, 4,848,373 and. 5,372,149. In addition to modifying the aroma of the leaf, fermentation can change either or both the color and texture of a leaf. Also during the fermentation process, evolution gases can be produced; oxygen can be taken up; the pH can change; and the amount of water retained can change. See, for example, U.S. Publication No. 2005/0178398 and Tso (1999, Chapter 1 in *Tobacco, Production, Chemistry and Technology*, Davis & Nielsen, eds., Blackwell Publishing, Oxford).

Cured, or cured and fermented, tobacco having reduced levels of DVTs can be further processed (e.g., cut, expanded, blended, milled or comminuted) and used in a smokeless tobacco composition. See, for example, U.S. Pat. Nos. 4,528, 993; 4,660,577; and 4,987,907. Smokeless tobacco compositions such as, without limitation, moist or dry smokeless tobaccos including snus-style products and snuff products, loose tobacco in a pouch or pack, chewing tobaccos, smokeless cigarettes, edible film strips, tobacco-coated toothpicks and extruded tobacco products can be produced that contain one or more of the varieties of tobacco described herein having reduced levels of DVTs or progeny thereof that have been selected for reduced levels of DVTs. See, e.g., U.S. Patent Publication Nos. 2005/0244521 and 2006/0191548 for descriptions of a number of smokeless tobacco compositions. In addition to tobacco having reduced levels of DVTs, smokeless tobacco compositions described herein can include other ingredients such as binders, plasticizers, stabilizers, and/or flavorings.

100% of the cured tobacco in a smokeless tobacco composition can be tobacco having reduced levels of DVTs. For example, 100% of the cured tobacco can be dark air cured, Burley (other than Burley tobacco designated TI 1406), air cured or dark fire cured tobacco. Alternatively, the cured tobacco in a smokeless tobacco composition can be a blend of one or more tobaccos having low levels of DVTs and one or more tobaccos that do not have reduced levels of DVTs. Exemplary tobaccos that do not have reduced levels of DVTs include, without limitation, LA B21, LN KY171, Basma, Galpao, Perique, Beinhart 1000-1, and Petico. As used herein, blends refer to combinations of tobaccos that have 80%-99% low-DVT tobacco (e.g., 80%-85%, 80%-90%, 85%-95%, 90%-99%, or 95%-99%). For example, 80% to 100% of the cured tobacco in an edible film composition or a dry or semi-moist smokeless tobacco composition can be from tobacco having reduced levels of DVTs, or 40% to 100% (e.g., 40%-60%, 50%-70%, or 60%-80%) of the cured tobacco in a moist smokeless tobacco composition can be from tobacco having reduced levels of DVTs.

In accordance with the present invention, there may be employed sensory evaluations as well as conventional plant breeding, plant biology and physiology, molecular biology, microbiology, and biochemical techniques within the skill of the art. The invention will be further described in the following examples, which do not limit the scope of the invention described in the claims.

EXAMPLES

Example 1

Seed Source 0.1 g of TI 1406 (PI 408940), KDH960 (PI 531523), KDH926 (PI 531521), KDH959 (PI 531522), TI 1068 (119208) and KY14 (PI 552477) seeds were obtained from the Oxford National Germplasm Repository (see ars-grin-.gov/npgs/holdings.html on the World Wide Web) (USDA) and multiplied in the greenhouse and field.

Example 2

Greenhouse Plant Production

Tobacco seeds were sown in pots containing Carolina Soil Mix. Three to five weeks after seeding, seedlings were transferred to pots and maintained in the greenhouse until leaf samples were collected. Plants were fertilized and sprayed for insects and diseases as needed.

Example 3

Leaf Production for Cured Leaf Samples

Transplant production, field practices and curing were conducted in accordance with those recommended for burley tobacco. Seeds were sown in float trays and maintained in transplant greenhouses for eight weeks. Seedlings were transplanted in the field and plants were topped. Plants were stalk-cut four to five weeks after topping and hung in a barn for air curing. After curing, leaves were stripped in one grade and bailed. Leaf samples were collected at stripping, dried at 40° C. and ground in a Wiley mill.

Example 4

Extraction of Tobacco Surface Compounds

Tobacco surface chemicals of green leaves were extracted from the plant by cutting a disk of 5.32 cm diameter from the leaf lamina of 10 plants from each tobacco type. The plants from which the leaf disks were obtained were grown in the field and/or the greenhouse, and samples were taken when the first flower started to open from leaves that were approximately 15-25 cm in length.

Each disk was gently washed for 30 seconds in 100 ml of methylene chloride in a single jar. The extract from all 10 leaves was filtered through a bed of anhydrous sodium sulfate, evaporated to dryness using $N_2$ and the residue was reconstituted in 10 ml of methylene chloride.

Example 5

TLC Analysis of Tobacco Surface Chemicals

TLC plates (Merck TLC Silica Gel 60, 2 mm, 10×20 cm) were pre-washed in chloroform-methanol (50:1, v/v), air dried and activated by heating at 120° C. for 30 min in an oven. Tobacco surface chemicals of green leaf extracts (FIG. 1A) or cured leaf extracts (FIG. 1B) were loaded (10 µl) on the plates using the CAMAG Automatic TLC Sampler 4. Plates were developed in a solvent chamber using chloroform-methanol (50:1, v/v) as the solvent. After air drying in a hood for 3 min, plates were sprayed with p-Anisaldehyde Ethanolic Sulfuric Acid (AESA) solution and heated with a hand dryer for color development of the bands.

Figure 1A:
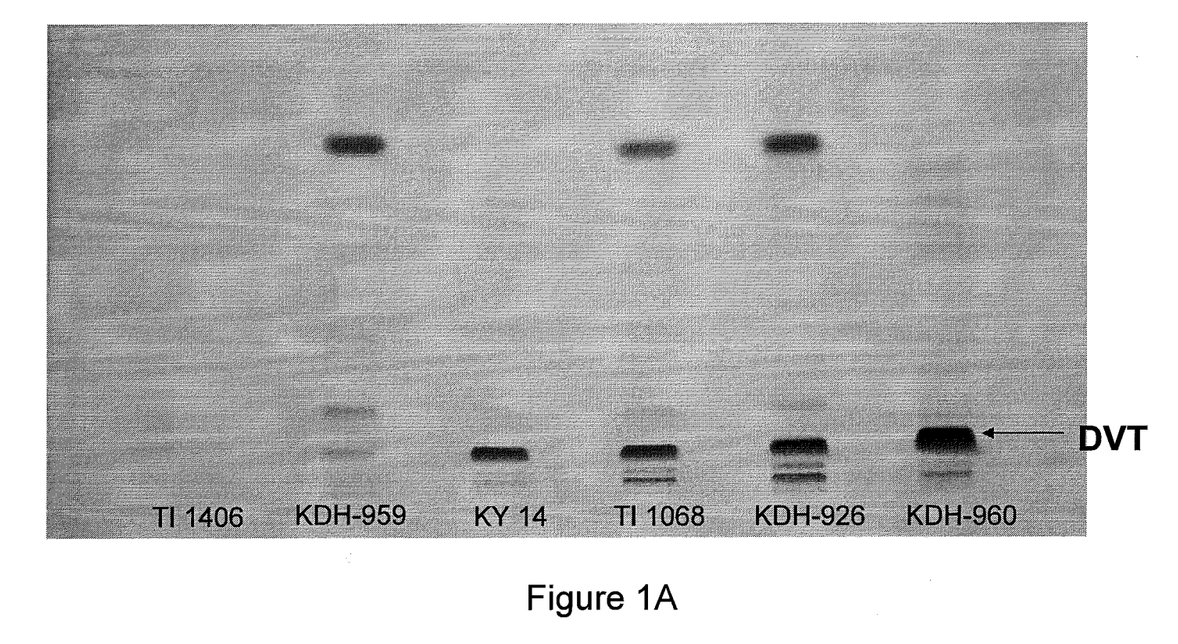
FIG. 1A shows leaf surface compounds from green leaf and FIG. 1B shows leaf surface compounds from cured leaf. The tobacco varieties are indicated at the bottom of the plate and the arrow shows the band corresponding to DVTs.
Figure 1B:
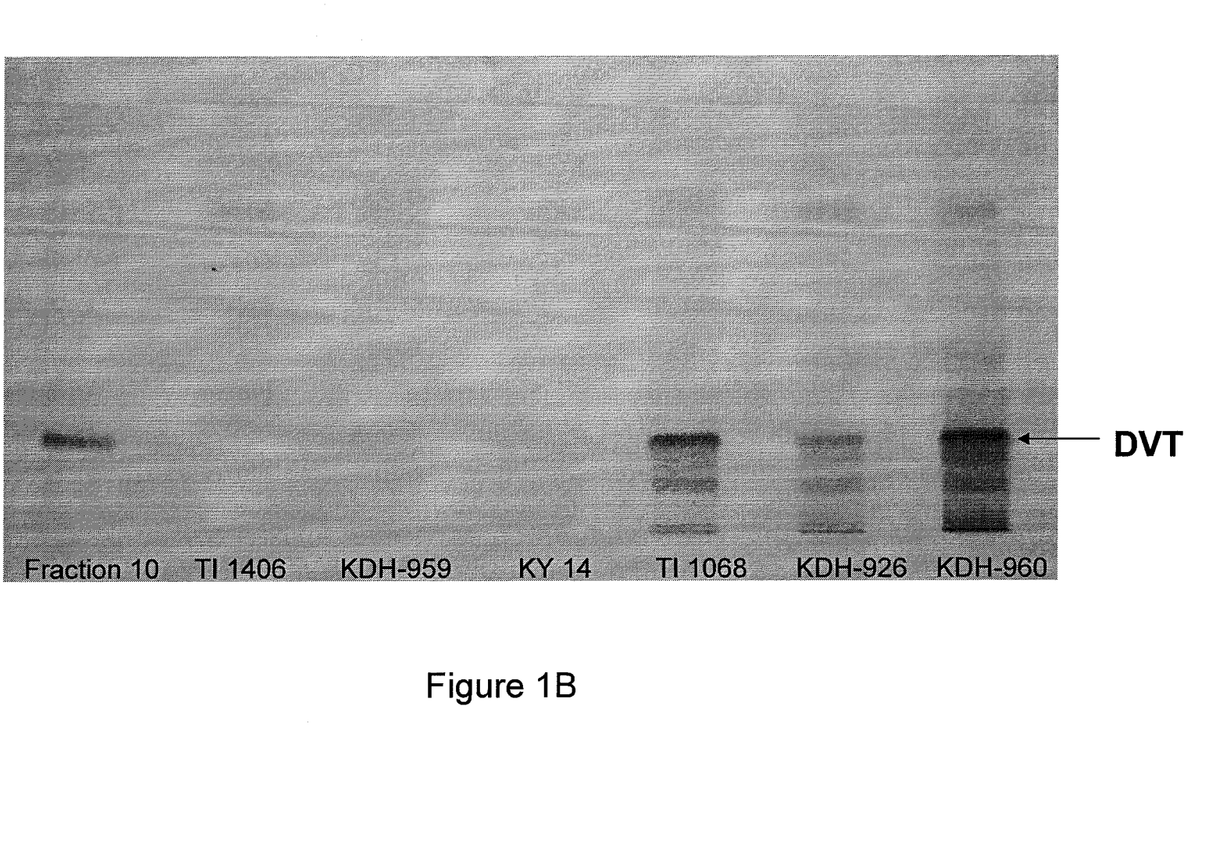

FIG. 1 shows the varying band intensities of DVTs observed in green leaf (Panel A) or cured leaf (Panel B) from a number of different tobacco varieties. No DVTs were detected in TI 1406 and very little detected in KDH959 compared to KY14. Further, TI 1068 had approximately the same amount of DVTs as does KY14, while KDH926 and KDH960 possessed more DVTs than KY14.

Example 6

Sensory Evaluation of Cured Tobacco Samples

Five experienced taste panelists were used to assess the sensation of bitterness in cured tobacco samples. Each panelist was presented with coded samples and asked to score the bitterness taste in the sample on a scale of 1 to 9, where 1 was considered to have the least amount of bitterness and 9 was considered to have the highest amount of bitterness. Panelists were required to rinse their palate with water and consume saltine crackers between each sample. The average results of the taste panel for each variety are shown in Table 2.

The levels of DVTs shown in Table 2 are from Nielsen & Severson (1990, *J. Agric. Food Chem.*, 38:467-471).

TABLE 2

DVT and Bitterness Levels

| Variety | Average Taste Panel Score | DVT Levels (alpha & beta; µg DVT/cm² green leaf tissue) | Bitterness Rank |
|---|---|---|---|
| KDH959 | 2.6 | 3.5 | 1 |
| TI 1406 | 3.1 | 0.2 ± <0.1 | 2 |
| KY14 | 4.6 | 38.1 ± 2.4 | 3 |
| KDH926 | 6.1 | 92.6 | 4 |
| TI 1068 | 7.1 | 75.1 ± 5.6 | 5 |
| KDH960 | 8.9 | 191 | 6 |

Example 7

Sensory Panel Evaluation of Smokeless Products

Two different taste tests were conducted on three different varieties of tobacco, with the same six participants used for both sessions. All six participants regularly use smokeless tobacco products and had participated in previous taste tests. Since the participants had previous experience, a training session to organoleptically define "bitterness" was not conducted.

In the first taste test (Tables 3 and 4), the tobacco samples (TI 1406, burley and a dark air-cured) were barn cured for 4-8 weeks, dried, slightly flavored with mint flavoring (all samples were flavored to a similar degree), cut to a particle size of 600 microns and then further milled to an average dry particle size of 200 microns. In the second taste test (Tables 5 and 6), the tobacco samples were barn cured for 4-8 weeks, dried and slightly flavored. The TI 1406 and the dark air-cured tobacco samples were cut to a particle size of 600 microns for the second taste test, while the burley tobacco sample was milled to an average particle size of 2 mm.

For both tests, tongue depressors were used to meter out the samples, the sample amount was left to the discretion of the participants, and participants were instructed to be consistent in the amount of samples to taste. Participants were asked to taste the samples in any order, rate the samples on a numeric scale of 1-15 for bitterness and for preference, and cleanse their palates with crackers and water between samples. To minimize peer influences, participants were also instructed to not express their reactions (verbal or facial).

The results of the sensory panel evaluation for bitterness are shown in Tables 3 and 5, with a lower number indicating less perceived bitterness. Tables 4 and 6 show the panelists' preference for each cured tobacco sample, with a higher number indicating a higher preference. TI 1406 was judged as having the least amount of bitterness and the highest preference by the taste panelists.

TABLE 3

Sensory Panel Evaluation for Bitterness

| Panelist | Dark Air Cured | TI 1406 | Burley |
|---|---|---|---|
| 1 | 11 | 11 | 7 |
| 2 | 14.5 | 5 | 1.3 |

TABLE 3-continued

Sensory Panel Evaluation for Bitterness

| Panelist | Dark Air Cured | TI 1406 | Burley |
|---|---|---|---|
| 3 | 11 | 9 | 12 |
| 4 | 6 | 9 | 12 |
| 5 | 12 | 3 | 11 |
| 6 | 12.5 | 5.3 | 12.3 |
| Total | 67 | 42.3 | 55.6 |

TABLE 4

Sensory Panel Preference

| Panelist | Dark Air Cured | TI 1406 | Burley |
|---|---|---|---|
| 1 | 2 | 2 | 5 |
| 2 | 1.5 | 9.5 | 11.5 |
| 3 | 5 | 7 | 3.5 |
| 4 | 12 | 7 | 3 |
| 5 | 2 | 5 | 2 |
| 6 | 6.2 | 10.5 | 4.2 |
| Total | 28.7 | 41 | 29.2 |

TABLE 5

Sensory Panel Evaluation for Bitterness

| Panelist | Dark Air Cured | TI 1406 | Burley |
|---|---|---|---|
| 1 | 10 | 6 | 7.5 |
| 2 | 2 | 4 | 2 |
| 3 | 13.2 | 9.5 | 13.5 |
| 4 | 10 | 2 | 12 |
| 5 | 11.5 | 5.7 | 10.6 |
| 6 | 10 | 3 | 9 |
| Total | 56.7 | 30.2 | 54.6 |

TABLE 6

Sensory Panel Preference

| Panelist | Dark Air Cured | TI 1406 | Burley |
|---|---|---|---|
| 1 | 3 | 11 | 7.5 |
| 2 | 12 | 2 | 14 |
| 3 | 3.5 | 3.5 | 7 |
| 4 | 2 | 6 | 1 |
| 5 | 5.3 | 12.5 | 4.5 |
| 6 | 3 | 9 | 3 |
| Total | 28.8 | 44 | 37 |

Example 8

GC/MS-SPME Analysis of Cured Leaf Samples

One gram of ground cured tobacco sample was placed into a 40 ml sampling vial containing 1 ml of saturated NaCl solution. Head space was equilibrated at 75° C. for 30 min in a water bath. SPME fiber (Supelco, Bellafonte, Pa.) 50/30 μm DVB/Carboxen/PDMS coating was exposed to the sample head space for 15 min for absorption. Samples were analyzed on a Varian instrument: Saturn 2200 GC/MS/MS equipped with a split-splitless injection port. Desorption of the SPME fiber was carried out for 5 min at 250° C. in splitless mode. GC column was a Phenomenex ZB-1ms: 0.25 mm (i.d.)×30 m immobilized thin film (0.25 μm). Mobile phase was helium: flow rate of 1 mL/min at constant pressure. Oven gradient temperature program: Initial temperature of 40° C. held for 3 min; ramped to 250° C. at 3° C. and held for 3 min; ramped to 320° C. at 3° C. and held for 3 min for a total run time of 102.33 min. Column clean up between injections was achieved by raising the oven temperature to 350° C. and held for 5 min. MS parameters were: Electron ionization at 70 eV; trap temperature of 150° C.; transfer line temperature was 170° C., and mass range was 40-600 amu. The compounds were identified by matching each spectrum generated with the NIST 05 Mass Spectral Library or in-house standards.

Figure 2:
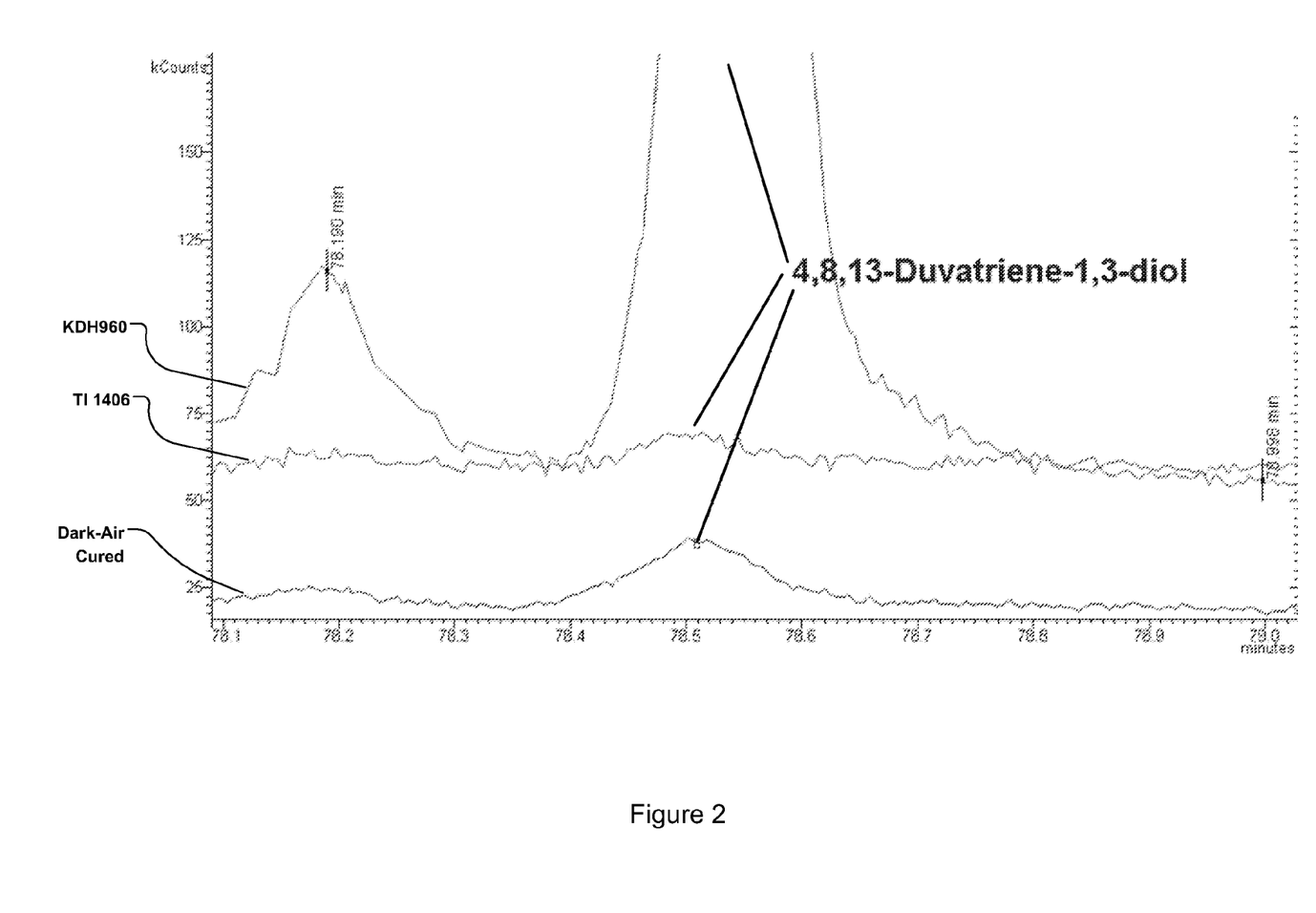
FIG. 2 is a partial chromatogram of a GC/MS-SPME analysis of DVTs in cured leaf tissue of TI 1406, KDH960 and a dark-air cured variety.
Figure 3A:
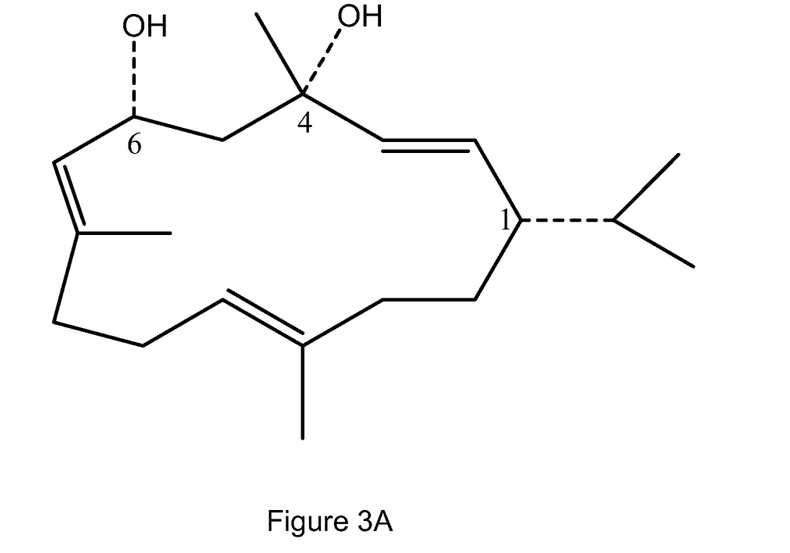
FIG. 3 shows the alpha isomer (Panel A) and beta isomer (Panel B) of DVT.
Figure 3B:
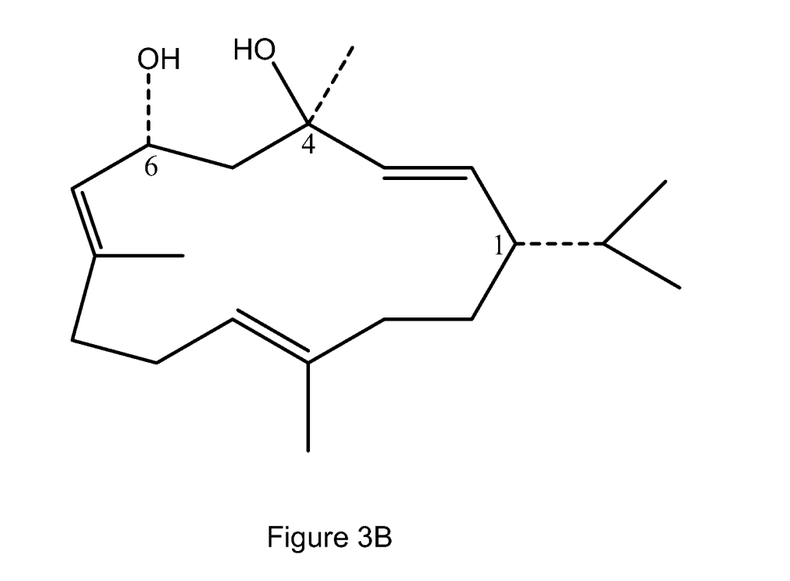

FIG. 2 shows a partial chromatogram of alpha- and beta-DVTs (it is noted that alpha- and beta-DVTs co-elute). Partial chromatograms demonstrated that other cembranoids or degradation products thereof including solanone, solavetivone, cembrene, and thunbergol were reduced in TI 1406.

Example 9

Materials

Chloroform, methylene chloride, and granular anhydrous sodium sulfate were obtained from EMD Chemicals, Inc., (Merck, Darmstadt, Germany). All chemicals were used without further purification. Cheesecloth (100% pure reagent grade) and filter paper were obtained from VWR International, Inc. (West Chester, Pa.). GC column was from Phenomenex, Inc. (Torrance, Calif.). Citric acid and caffeine (food grade), tartaric acid, and Celite (CAFAII) were from Sigma-Aldrich (ST. Louis, Mo.). Methanol HPLC grade was obtained from Mallinckrodt Baker, Inc. (Phillipsburg, N.J.). Sodium chloride non-iodized (Morton's International), sugar (pure cane granulated, Domino Foods, Inc.), and crackers (unsalted), were obtained from a local grocery store. Tobacco used in this study were field grown or green house grown in Winchester, Ky. using normal production techniques.

Example 10

Extraction of Tobacco Leaf Surface Chemicals

Tobacco leaf surface chemicals of green and cured leaves were extracted by cutting a disk of 5.32 cm diameter from the leaf, one leaf per plant. Samples were taken from the fifth to the eighth leaf from the top. Disks were collected from 10 plants for each tobacco type in the field. The green leaves were harvested when plants were at the flowering stage. Each disk was washed continuously for 30 seconds in 100 ml of methylene chloride in a mason jar wrapped with aluminum foil. The extract was filtered through a bed of anhydrous sodium sulfate, evaporated to dryness using $N_2$ and the residue was reconstituted in 10 ml of methylene chloride. All steps were taken to minimize the extract exposure to light. It is noted that the method disclosed herein resulted in a greater yield of DVTs than did the method of Nielsen & Severson (1990, *J. Agric. Food Chem.*, 38:467-471).

Example 11

Isolation of DVTs

DVTs were isolated from trichome exudates of the tobacco germplasm KDH 960 grown in the green house and used as the reference material in the quantitation of DVTs in the field tobacco leaves. The extraction procedures were those described by Chang & Grunwald (1976, *J. Lipid Res.*, 17:7-11). Batches of twenty leaf samples were collected for extraction per set of cheesecloths. Cheesecloth wipes were 46 cm×92 cm (18"×36"). Leaf trichome exudates were extracted as follows.

Four cheesecloths were pre-extracted with chloroform ($CHCl_3$) and then air dried. Each cloth was folded into four layers. Two of the folded cheesecloths, one on top of the other, were pinned to two bread boards. Each tobacco leaf was placed between the fixed sets of pre-extracted cheesecloth and the top board was firmly rolled using a large rolling pin. Each leaf was carefully removed and replaced after rolling 10-12 times, where one roll consisted of one forward and one backward stroke. Each set of cheesecloth was then extracted with 300 mL of chloroform, in a 1.0 L Erlenmeyer flask with cap, by shaking for 60 min at 200 rpm (New Brunswick Scientific C78 Water Bath Shaker, Edison, N.J.) at ambient temperature. The extract was then filtered into a 1000 mL recovery flask (24/40 Joint) through a bed of celite to remove debris. The cloths were again extracted two more times using 200 mL chloroform. The extracts were combined and concentrated to 250 mL on a rotary evaporator (BUCHI Rotavapor, R-205 with vacuum controller V-805, Buchi Corporation, New Castle, Del.; with a water chiller, WKL 230, Lauda, Germany), then washed with 100 mL of 1.0 M tartaric acid. The organic phase was separated with a 500 mL reparatory funnel and filtered through a bed of anhydrous granular sodium sulfate, then evaporated to dryness using the rotary evaporator. The residue was transferred to a 5 mL brown storage vial and blown down until free of solvent using $N_2$ and stored in the refrigerator. Analyses showed the DVT concentration was 81.61% pure, with 68% of the yield being alpha- and beta-DVTs.

Example 12

Quantitation

Figure 4:
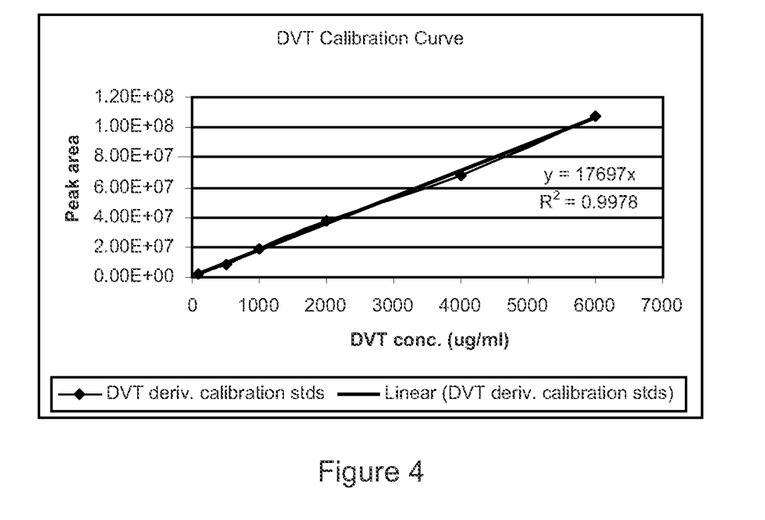
FIG. 4 shows a calibration curve of butylboronic derivatives of alpha- and beta-DVTs.

A six point alpha- and beta-DVT calibration curve ranging from 100 to 6000 μg/mL in methylene chloride was prepared from a stock solution of the DVT isolate (81.61% purity; FIG. 4). The concentrations were weight adjusted for the purity of the isolate. Each standard and tobacco sample was derivatized using 500 μL of solution or sample in methylene chloride, with 500 μL of excess butylboronic acid in pyridine. Standards and samples were prepared in replicates and each replicate analyzed two times. Because DVT response was not linear in the range below 5 μg/mL to 100 μg/mL, where necessary, some tobacco samples were concentrated or diluted such that the MS responses were within the calibration range.

Example 13

GC-MS Analysis of DVTs

Samples were analyzed on a Varian Saturn 2200 GC-MS equipped with a split-splitless injection port. Injection temperature was 250° C. in split mode 1:100. GC column was a Phenomenex ZB-5: 0.25 mm (i.d.)×30 m, bonded film (0.25 μm). Mobile phase was ultra high purity (UHP) helium with a flow rate of 1.0 mL/min at constant pressure. Oven gradient temperature program: Initial temperature of 150° C. held for 0.0 min; ramped to 280° C. at 4° C. increments and held for 10 min; ramped to 320° C. at 80° C. increments and held for 5.0 min. Total data collection time was 47.5 min. Column clean up between injections was achieved by raising the oven temperature from 280° C. to 320° C. and held for 5 min. MS parameters were: electron ionization at 70 eV; trap temperature of 150° C.; transfer line temperature was 260° C., and mass range was 33-400 amu, with a scan delay of 2.0 min to avoid solvent effect on chromatogram.

Example 14

Sensory Evaluations

Taste Panel Training

Panelists were trained using three concentrations of sugar (sweet), NaCl (salt), citric acid (sour), and caffeine (bitter) (Dunkel et al. (2007, *J. Agric. Food Chem.*, 55:6712-9)) as indicated in Table 7. Solutions of decreasing concentration were prepared such that each was half the concentration of the preceding one. Before the solutions were tasted, panelists were instructed to rinse their mouths with purified water and consume crackers. Each solution was presented to the panelist in increasing order of concentration (Tamura et al. (1989, *Agric. Biol. Chem.*, 53:1625-1633)). After tasting the solutions, a reference tobacco sample (KY14, ground to a standard mesh size) was evaluated and assigned a score of 5 for bitterness. KY14 was later used as the control in all tobacco evaluation sessions.

Training of the panel was carried out for eight weeks with three sessions per week using physical (tobacco samples) and chemical (food grade from Sigma-Aldrich, Inc.) references to help panelist establish common data points. Panelists were trained to recognize the same concentrations of reference compounds (Belitz & Grosch (1999, *Food Chemistry*, pp 33-7 & 763-4)) and to assign the same scores (Table 7). The lowest concentration was given a score of 1, the middle concentration 5 and the highest 9 (Table 7). During the training sessions, the objective of the sensory test was explained to the panelists and they agreed upon the lexicon. Of ten trained panelists, one proved unreliable and data from that panelist was excluded.

During all training, panelists were asked to refrain from using tobacco products for at least one (1) hr before any session (ASTM Standards). Panelists were instructed that no talking was allowed until after the tests were completed. To ensure panelist performed to the best of their ability, it was recommended that they be available at every training and evaluation sessions. Three 45 min sessions of 10 people each were held per week.

TABLE 7

Chemical sensory references and scores

| | | Score | | |
|---|---|---|---|---|
| | | 1 | 5 | 10 |
| Attribute | Chemical Reference | Concentrations (%, w/v) | | |
| Sweet | Sucrose (Domino's) | 1.0 | 2.0 | 4.0 |
| Salt | Sodium chloride (Morton's) | 0.15 | 0.3 | 0.6 |
| Acid/Sour | Citric Acid | 0.25 | 0.5 | 1.0 |
| Bitter | Caffeine | 0.035 | 0.07 | 0.14 |

Taste Panel Evaluation

A taste test was designed to determine and evaluate the bitterness (descriptive analysis) of tobacco leaf samples. Six to nine trained taste panelists (Grub (1998, In *Flavourings* by Ziegler & Ziegler, eds., pp. 513-524, Wiley-VCH Verlag GmbH, Weinheim, Germany); Tamura et al. (1989, *Agric. Biol. Chem.*, 53, 1625-1633)) were available per session to assess the perceived bitterness of the cured tobacco samples.

Each panelist was presented with the samples and asked to score the bitter taste in the sample on an interval scale of 1 to 9 (Adams (1985, In *Characterization and measurement of flavor compounds*, by Bills & Mussinan, eds., ACS Symposium Series 289, American Chemical Society, Washington D.C., pp 11-25); Meilgaard et al. (1991, Sensory evaluation techniques, 2$^{nd}$ Ed., CRC Press, Boca Raton, Fla.)). A score of one was to be given by a panelist if the sample was considered least bitter and a score of nine was given if the sample was considered the most bitter. Panelists were instructed to wait about 5-10 minutes between samples, during which time they rinsed their palate with water and saltine crackers (Lawless & Gillette (1985, In *Characterization and measurement of flavor compounds*, by Bills & Mussinan, eds., ACS Symposium Series 289, American Chemical Society, Washington D.C., pp 26-41)).

All samples were coded with random three-digit numbers and dried and ground to a standard mesh size. Tobacco samples were presented such that visual differences between samples were not apparent to the panelists and were tasted by the panelists using moistened tooth picks. Each sample was evaluated three times over three consecutive sessions. All attempts were made to minimize the environmental influences such as smells, light, noise, and all sessions were held at the same time each day (American Society for Testing and Materials (ASTM), Technical Committee E18, Standards E18.01-E18.06).

Taste Panel Results

Figure 5:
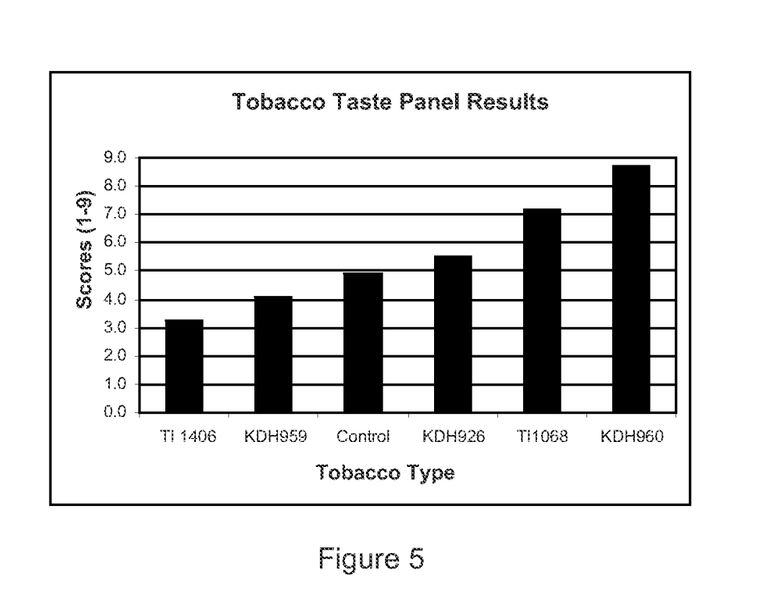
FIG. 5 shows a graph of the taste panel results described in Part B of the Examples, where 1 is low bitter intensity and 9 is high bitter intensity.

FIG. 5 shows the results of the taste panel for each of the tobacco types tested, where 1 is low bitter intensity and 9 is high bitter intensity. As can be seen from FIG. 5, TI 1406 and KDH959 have the lowest score for bitterness, while TI 1068 and KDH960 have the highest score for bitterness.

Example 15

Figure 6:
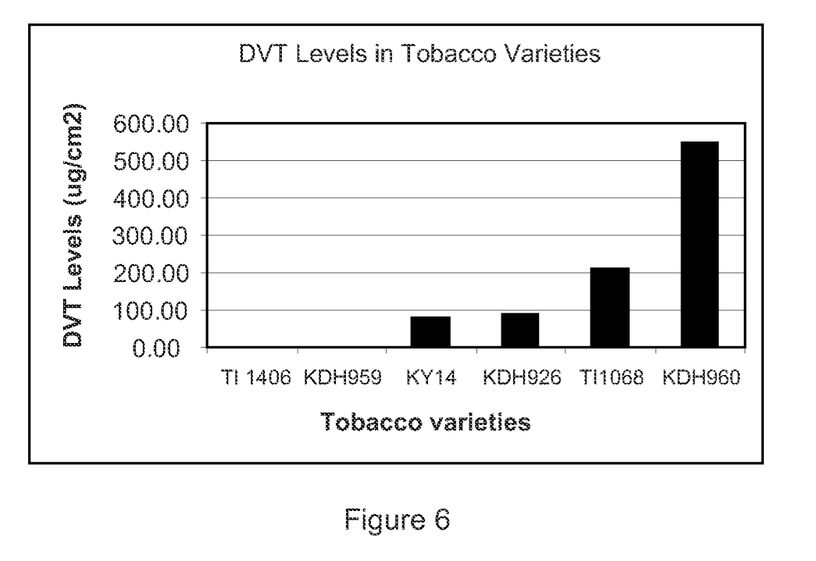
FIG. 6 shows a graph of the average alpha- and beta-DVTs concentrations (μg/cm$^2$) in the indicated tobacco varieties.

DVT Levels in Green Leaves and Bitterness in Cured Leaves from Field-Grown Tobacco Plants Tobacco plants from varieties TI 1406, KDH959, HY14, KDH926, TI 1068 and KDH960 were grown in the field according to the 2007 Kentucky Tobacco Production Guide. Green leaves were harvested and alpha- and beta-DVTs present on the leaf surface were measured as described above in Example 4. FIG. 6 shows the average DVT concentration (alpha- and beta-DVT; μg/cm$^2$) in the green leaves of different tobacco varieties. As can be seen in FIG. 6, the levels of DVTs in green leaf tissue from TI 1406 and KDH959 were very low.

The bitterness of the cured tobacco leaves from the same varieties was evaluated by a sensory panel as described in Example 14. The results of the sensory evaluation are shown in Table 8.

TABLE 8

Sensory data for tobacco
Statistical Significance of Bitter and DVTs data (p < 0.05)

| | Mean Bitterness Value | | Mean DVT Levels (μg DVT/cm$^2$ green leaf tissue) | |
|---|---|---|---|---|
| TI 1406 | 3.2 | a | 0.2 | a |
| KDH959 | 4.1 | a, b | 0.00 | a |
| KY14 | 4.9 | a, b, c | 81.4 | b |
| KDH926 | 5.5 | a, b, c | 90.1 | b |
| TI 1068 | 7.2 | b, c | 207.9 | c |
| KDH960 | 8.8 | c | 549.5 | d |

Average sensory scores followed by the same letter are not significantly different (p < 0.05 level) according to Kruskal-Wallis multilple comparisons test.
Average DVT levels followed by the same letter are not statistically different (p < 0.05 level) according to Tukey's HSD test.

Figure 7:
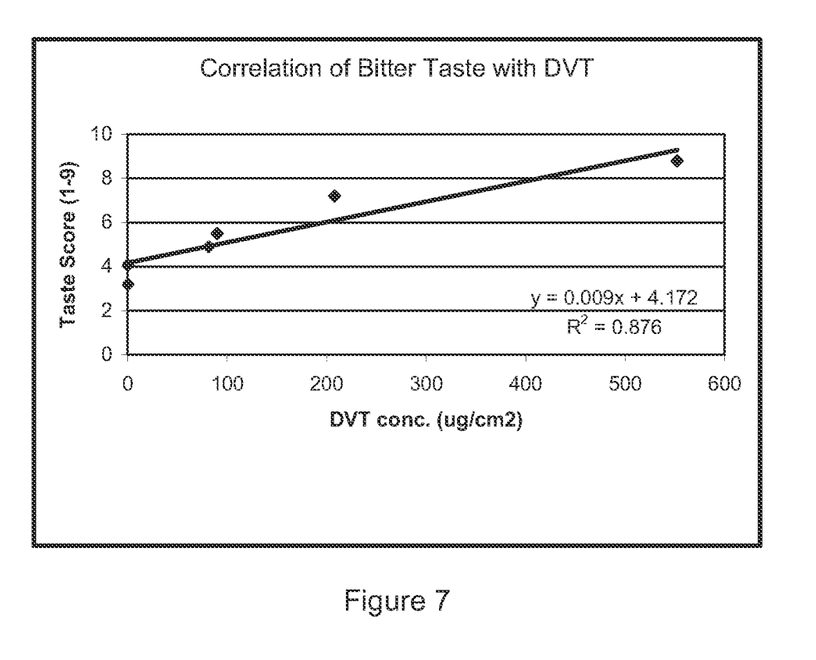
FIG. 7 is a graph showing the correlation between bitter taste and DVT levels. Like reference symbols in the various drawings indicate like elements.

The correlation between bitter taste and the levels of DVTs in green leaf tissue is shown in FIG. 7. As can be seen from the linearity of the data, there is a direct statistically significant correlation ($R^2$=0.876, at p≤0.05) between the level of DVTs and bitter taste.

Example 16

Washing with a Food-Grade Solvent

Ten leaves were collected from each of the tobacco varieties (TI 1406, KY171, KDH960) at the green mature leaf stage and at the cured stage. The leaves were all split longitudinally. One half of each leaf, without any treatment, was dried at 37° C. The other half was washed to remove the leaf surface trichome exudates containing the cembranoids, together with other compounds as described herein. Leaves were washed three times for 30 sec in three 1 L volumes of 95% pure grain alcohol (Everclear, Luxco Distilling Co., St. Louis, Mo.). Leaves were washed at room temperature, by gentle agitation, drained then dried at 37° C. The washed and unwashed dried leaves were then evaluated by a trained sensory panel as described herein. The results are shown in Tables 9 and 10 below.

TABLE 9

Taste panel scores for washed vs. non-washed green tobacco leaves

| Sample | Average Score ± Standard Deviation |
|---|---|
| Washed | |
| TI 1406 | 2.2 ± 0.7 |
| KY171 | 2.3 ± 0.5 |
| KDH960 | 2.3 ± 0.6 |
| Unwashed | |
| TI 1406 | 2.6 ± 0.6 |
| KY 171 | 6.5 ± 1.5 |
| KDH 960 | 8.1 ± 0.1 |

TABLE 10

Taste panel scores for washed vs. non-washed cured tobacco leaves

| Sample | Average Score ± Standard Deviation |
|---|---|
| Washed | |
| TI 1406 | 3.0 ± 1.3 |
| KY171 | 4.2 ± 0.3 |
| KDH960 | 4.5 ± 1.6 |

TABLE 10-continued

Taste panel scores for washed vs. non-washed cured tobacco leaves

| Sample | Average Score ± Standard Deviation |
|---|---|
| Unwashed | |
| TI 1406 | 2.8 ± 1.1 |
| KY 171 | 5.7 ± 0.6 |
| KDH 960 | 8.3 ± 0.3 |

Washing the leaves of KY 171 and KDH 960 with a food grade solvent such as, without limitation, ethanol, ethyl acetate, butyl acetate, water, acetic acid, propanol, or any combination thereof significantly reduced the bitterness score of those tobaccos as determined by a trained taste panel. There was no significant difference in the taste between the washed samples of TI 1406, KY 171 and KDH 960. In addition, there was no significant difference between the washed and unwashed TI 1406. Statistical significance was evaluated using the Mann-Whitney U-test.

Example 17

Film Strips Containing Tobacco with Reduced Levels of DVTs

Tobacco film strips can be made using ingredients shown in Table 11. For example, tobacco film strips can be made by mixing 50 grams of K-3 (60%), K-100 (35%) and K4M (5%) grades of hydroxypropylmethyl cellulose (HPMC) from Dow Chemical in a beaker containing 450 grams of well agitated, deionized water which has been heated to 180° F. While mixing, 40 grams of finely ground tobacco are added to the HPMC solution along with 15 grams of microcrystalline cellulose (FMC), 17 grams of starch (B-700 from Grain Processing Corp.), 16 grams of glycerine, 0.8 grams of polysorbate 80 (Unichema), and 4 grams of propylene glycol monostearate (PGMS from Danisco). Ten grams of cinnamon flavor and 2 grams of sucralose (artificial sweetener) are added to the solution when the temperature has dropped below 100° F. Two grams of sodium carbonate are added to adjust the pH to approximately 7.5. Once all the ingredients have been added and have been uniformly dispersed, the mixture is placed in a water bath and, with continued mixing for 30 minutes, is reduced to 65° F. Additional water is added as required to obtain a Brookfield viscosity of 5,000 centipoise at a temperature of 65° F., resulting in solution solids of approximately 17% w/w.

A portion of this tobacco-containing solution is then spread on a glass plate using a draw-down blade with a fixed gap of 15 mils (0.015 inches). The glass plate is placed in an air circulating laboratory oven preset at a temperature of 170° F. After 30 minutes, the glass plate is removed from the oven, cooled to room temperature, and the dry film with a thickness of 2.5 mils (0.0025 inches) is removed from the glass plate. The film is then cut into smaller pieces suitable for placing in the mouth. A 1.0 inch by 1.25 inch section of the film typically disintegrates in the mouth in less than one minute, thereby releasing the flavor, sweetener, and tobacco. The tobacco content of this film on a dry weight basis is 25%.

TABLE 11

| Tobacco film | | |
|---|---|---|
| | Exemplary (%) | Preferred (%) |
| Water soluble polymer | 10-70 | 20-65 |
| Tobacco | 1-90 | 20-40 |
| Flavor | 1-40 | 5-15 |
| Sweetener | 0.2-6 | 2-5 |
| Fiber (Soluble or insoluble) | 2-40 | 5-20 |
| Plasticizer | 1-40 | 5-15 |
| Surfactants | 0.01-20 | 0.1-1 |
| Starch/Maltodextrin | 1-40 | 10-20 |
| Lubricant | 0.5-10 | 1-3 |

A sensory taste panel is used to evaluate monolayer or bi-layer film strips containing TI 1406, KDH 959, TI 1068 or KDH 960 tobacco. In addition, tobacco-containing film strips are evaluated for the level of DVTs.

Example 18

Tobacco-Coated Toothpicks

Toothpicks coated with tobacco are produced. The coating is made using the ingredients shown in Table 12.

TABLE 12

| Toothpick Coating | | |
|---|---|---|
| Ingredient | Exemplary (%) | Preferred (%) |
| Water soluble polymer | 0-70 | 0.1-25 |
| Tobacco | 1-90 | 5-40 |
| Flavor | 0-40 | 0.5-15 |
| Sweetener | 0-6 | 0.1-2 |
| Fiber (soluble and insoluble) | 0-40 | 0.1-20 |
| Plasticizer | 1-90 | 10-75 |
| Starch/Maltodextrin | 1-90 | 10-40 |
| Colorant | 0-2 | 0.2-1.5 |

Briefly, water is heated to 180° F., and solids such as the water soluble polymer and the tobacco are vigorously mixed into the water. Other ingredients such as the plasticizers are then vigorously mixed into the solution until the solids are completely dissolved and/or well-dispersed. The solution is cooled. Flavoring(s), if desired, can be added after cooling. The solution is held under a vacuum until sufficiently degassed and then cooled to 80° F.

Approximately ⅔ to ¾ of a conventional wooden or plastic toothpick is rolled in, wrapped in, dipped in or coated with the tobacco-containing solution and allowed to dry. A sensory taste panel is used to evaluate toothpicks coated with a suspension that includes TI 1406, KDH959, TI 1068 or KDH960 tobacco. Tobacco-coated toothpicks also are evaluated for the level of DVTs.

Example 19

Tablets and Extruded Products Containing Tobacco

TABLE 13

| Tobacco Powder for Tablets or Extrusion | | |
|---|---|---|
| Ingredient | Exemplary (%) | Preferred (%) |
| Water soluble polymer | 0-70 | 0.1-25 |
| Tobacco | 1-90 | 20-40 |
| Flavor | 0.1-40 | 1-15 |

TABLE 13-continued

Tobacco Powder for Tablets or Extrusion

| Ingredient | Exemplary (%) | Preferred (%) |
|---|---|---|
| Sweetener | 0-25 | 0.1-15 |
| Plasticizer | 0.1-40 | 1-15 |
| Starch/Maltodextrin | 0-75 | 10-50 |
| Lubricant | 0-10 | 0.1-3 |
| Colorant | 0-10 | 2-7 |

Tablets and/or extruded products containing tobacco are made by initially combining formulary ingredients in a manner to form a granulation. The process of making a granulation may include the steps of preparing a binding solution and subsequently combining with dry ingredients.

Preparation of Binding Solution

Ingredient amounts as indicated in Table 13 are weighed out into separate containers. One or more water soluble polymers (e.g., gum Arabic pre-hydrated) are slowly added to the water and mixed under high shear agitation in a stainless steel vessel. After complete dissolution, maltodextrin (M 585, Grain Processing Corporation) is added slowly to the water. Once the maltodextrin is completely dissolved, sweetener is added slowly and mixed thoroughly to ensure complete dissolution. Formulary amounts of flavorings (e.g., peppermint and spearmint) as shown in Table 13 are added to the binding solution. The entire mixture is homogenized with a homogenizer.

Preparation of Dry Ingredients and Subsequent Granulation

The formulary amounts of tobacco powder as shown in Table 13 are blended together and placed in the product bowl of a fluid bed chamber. The fluid bed coater is used to apply the binding solution to the dry ingredient blend to form the final granulation. Once the dry ingredients are fluidized in the fluid bed chamber and achieved an adequate temperature, the binding solution is slowly sprayed onto the dry ingredients to form the granulation.

Product Formation

Tablets containing tobacco are made by combining granulated material with an appropriate amount of lubricant, and processing the combination into a tablet shape with a tablet press or the like. Dissolution rates of tablets provided in this manner can be controlled by utilizing the appropriate compression and fill parameters on the tablet press.

Alternatively, extruded products containing tobacco are made by combining granulated material with an appropriate amount of plasticizer (e.g., water) and processing the combination into an extruded shape (e.g., a rod) with an extruder fitted with an appropriately shaped die.

Example 20

DVTs in Cultivated Tobacco Types

Table 14 shows the level of DVTs in the indicated tobacco types (as determined using the methods described herein in Example 4).

TABLE 14

DVTs of commercial tobaccos

| Green Leaf Field Sample | Tobacco Type | Average DVT Content ($\mu g/cm^2$) |
|---|---|---|
| KY171 | Dark | 128.92 |
| TN 90LC | Burley | 86.63 |
| TN 86LC | Burley | 66.11 |
| KT 204LC | Burley | 52.33 |
| Beinhart 1000 | Cigar | 45.02 |
| NLMLC | Dark | 101.38 |
| KT D6LC | Dark | 143.36 |
| K326 | Flue cured | 89.89 |
| NC 71 | Flue cured | 85.72 |
| Maryland 609 | Maryland | 44.78 |
| Basma | Oriental | 130.24 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing a plant variety, comprising the steps of:
   crossing first tobacco plants with second tobacco plants to produce progeny plants, said first tobacco plants having less than 20 µg DVTs/cm² green leaf tissue and said second tobacco plants having greater than 20 µg DVTs/cm² green leaf tissue;
   allowing said progeny plants to self-pollinate for at least one generation;
   selecting, in at least one generation, for a) plants having less than 20 µg DVTs/cm² green leaf tissue and
   b) plants, wherein cured tobacco from said plants has reduced levels of DVTs relative to cured tobacco from plants of the variety designated KY14.

2. A method of producing a plant variety, comprising the steps of:
   mutagenizing tobacco plant tissue;
   propagating plants derived from said mutagenized plant tissue by self-pollination for at least one generation;
   selecting, in at least one generation, for a) plants having less than 20 µg DVTs/cm² green leaf tissue and
   b) plants, wherein cured tobacco from said plants has reduced levels of DVTs relative to cured tobacco from plants of the variety designated KY14.

3. A method of producing a plant variety, said method comprising the steps of:
   crossing first tobacco plants with second tobacco plants to produce progeny plants, wherein tissue from said first tobacco plants has significantly reduced bitterness in a sensory panel evaluation relative to tissue from plants of the variety designated KY14 and wherein tissue from said second tobacco plants does not have significantly reduced bitterness in a sensory panel evaluation relative to tissue from plants of the variety designated KY14;
   allowing said progeny plants to self-pollinate for at least one generation; and
   selecting, in at least one generation, for a) plants having less than 20 µg DVTs/cm² green leaf tissue and
   b) plants, wherein cured tobacco from said plants has reduced levels of DVTs relative to cured tobacco from plants of the variety designated KY14.

4. A method of producing a plant variety, said method comprising the steps of:
- crossing first tobacco plants with second tobacco plants to produce progeny plants, wherein cured tobacco from said first tobacco plants has reduced levels of DVTs relative to cured tobacco from plants of the variety designated KY14 and wherein cured tobacco from said second tobacco plants does not have reduced DVTs relative to cured tobacco from plants of the variety designated KY14;
- allowing said progeny plants to self-pollinate for at least one generation; and
- selecting, in at least one generation, for a) plants having less than 20 µg DVTs/cm$^2$ green leaf tissue and
- b) plants, wherein cured tobacco from said plants has reduced levels of DVTs relative to cured tobacco from plants of the variety designated KY14.

5. The method of claim 1, 2, 3 or 4, wherein said selecting step comprises selecting at the $BC_1$, $BC_2$ or $BC_3$ generation.

6. The method of claim 1, 2, 3 or 4, wherein said selecting step comprises selecting at the $F_2$ or $F_3$ generation.

7. The method of claim 3, wherein said sensory panel evaluation is performed on green leaf tissue.

8. The method of claim 3, wherein said sensory panel evaluation is performed on cured tobacco.

9. The method of claim 1, 2, 3 or 4, wherein said variety has reduced levels of solanone, solavetivone, cembrene, or thunbergol.

10. The method of claim 1, 2, 3 or 4, further comprising the step of curing green leaf tobacco produced by plants of said variety.

11. The method of claim 1, 2, 3 or 4, wherein said first and said second tobacco plants are dark tobacco plants.

* * * * *